United States Patent [19]

Weder et al.

[11] 4,438,052

[45] Mar. 20, 1984

[54] PROCESS AND DEVICE FOR PRODUCING BILAYER VESICLES

[75] Inventors: Hans G. Weder, E. Merck, Postfach 4119, 6100 Darmstadt 1, Fed. Rep. of Germany; Otmar Zumbühl, Wolfenshiessen; Reto Schwendener, Arosa, both of Switzerland; Manfred Milsmann, Bielefeld, Fed. Rep. of Germany

[73] Assignee: Hans Georg Weder, Zurich, Switzerland

[21] Appl. No.: 224,993

[22] Filed: Jan. 14, 1981

[30] Foreign Application Priority Data

Jan. 16, 1980 [CH] Switzerland .............................. 340/80

[51] Int. Cl.³ ....................... B01J 13/02; B01D 13/00
[52] U.S. Cl. ................................. 264/4.6; 210/321.2; 424/37; 424/38; 424/43; 424/85; 424/88; 424/172; 436/829
[58] Field of Search ..................... 252/316; 424/36, 38; 210/321.2; 264/4.6; 436/829

[56] References Cited

U.S. PATENT DOCUMENTS

| | | |
|---|---|---|
| 2,664,395 | 12/1953 | Marchand ......................... 210/321.2 |
| 3,957,971 | 5/1976 | Oleniacz ................................ 424/70 |
| 4,217,344 | 8/1980 | Vanlerberghe et al. ........ 252/316 X |
| 4,224,179 | 9/1980 | Schneider ............................ 252/316 |
| 4,235,871 | 11/1980 | Papahadjopoulos et al. ... 252/316 X |
| 4,323,455 | 4/1982 | Tanaka et al. .................... 210/321.2 |

FOREIGN PATENT DOCUMENTS 2405733 6/1979 France .............................. 210/321.2

OTHER PUBLICATIONS

Biochim. Biophys. Acta, 457, 259–302 (1976).
CRC Critical Reviews in Toxicology 6, 25–29 (1978).
Ann. Rev. Biophys. Bioeng. 9, 467–508 (1980).
Biochemistry 18, 4173–4176 (1979).

Primary Examiner—Richard D. Lovering
Attorney, Agent, or Firm—Millen & White

[57] ABSTRACT

A process for producing bilayer vesicles from a colloidal solution comprising mixed micelles of a bilayer-forming substance and a detergent, comprises removing the detergent from the micelle-containing colloidal solution by means of flow-through dialysis whereby the colloidal solution is dialyzed against a dialysis liquid in a chamber whose walls are at least partially formed by a semi-permeable membrane, wherein the dialysis liquid is moved along the outer side of the semi-permeable membrane at a velocity such that the detergent concentration in the dialysis liquid, on at least 90% of the active surface of the membrane, is at most 10% of the detergent concentration in the micelle solution in contact with the other side of the membrane, and wherein a homogeneous detergent concentration is maintained in the micelle solution by the movement of the latter.

7 Claims, 2 Drawing Figures

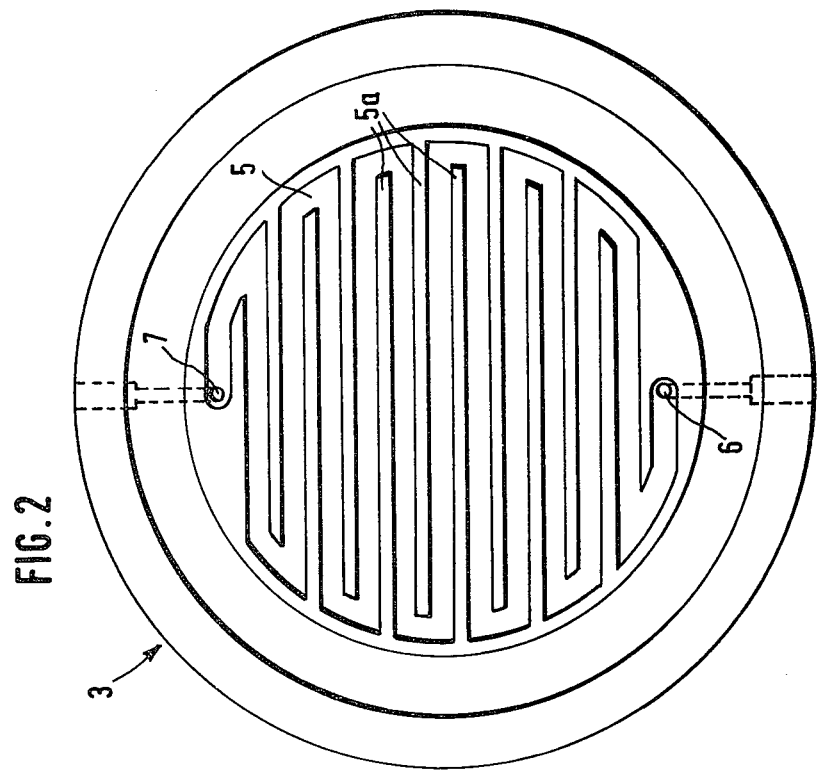
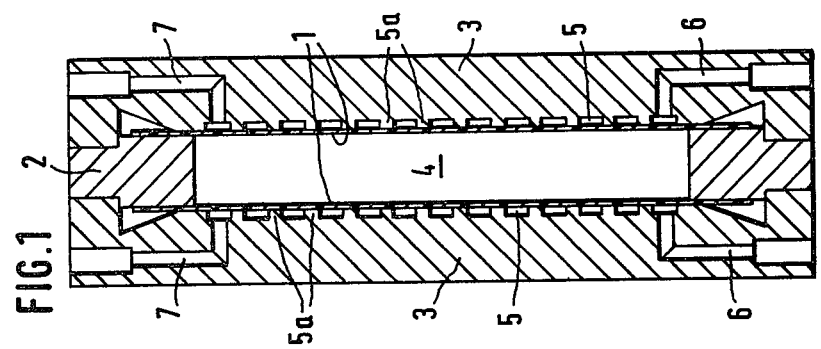

PROCESS AND DEVICE FOR PRODUCING BILAYER VESICLES

BACKGROUND OF THE INVENTION

The present invention relates to a process for producing bilayer vesicles by forming mixed micelles in a colloidal solution from a bilayer-forming substance and a detergent, and removing the detergent by means of flow-through dialysis.

Substances which are capable of forming bilayers (i.e., double layers) in the aqueous phase are known, for example phospholipids, such as lecithin. These bilayers are frequently in the shape of small hollow spheres which are hereinafter referred to as bilayer vesicles.

Known processes for producing bilayer vesicles, such as subjecting bilayer-forming substances to ultrasound, injecting bilayer-forming substances dissolved in organic solvents into an aqueous medium, removing detergents from micelle solutions (i.e., solutions of mixed micelles of bilayer-forming substance and detergent) by means of gel chromatography, and conventional dialysis [compare Biochim. Biophys. Acta 457, 259–302 (1976), CRC Critical Reviews in Toxicology 6, 25–79 (1978)], produce bilayer vesicles with undesired properties. The main disadvantages of such processes are characterized by the inclusion of organic solvents in the bilayer vesicles, the degradation of the bilayer-forming substance, the formation of multi-lamellar structures and, in particular, the formation of vesicles which are nonhomogeneous in size (20 to 200 nm in diameter). Furthermore, undesired dilution effects can occur and these necessitate a subsequent concentration process. If bilayer vesicles are employed as medicament carriers and/or as pharmaceutical preparations, the resultant plasma clearance and distribution in the organs are determined above all by the homogeneity of the vesicles and the vesicle size. Multi-lamellar heterogeneous structures are rapidly absorbed, in particular, by the spleen and the liver and are no longer available to the organism as a pharmodynamically active substance [Biochim. Biophys. Res. Comm. 63, 651–658 (1975)]. The extent and course of this process, and the interaction of the vesicles at the cellular level, can be controlled by selection of suitable lipid composition and morphology (size) of the vesicles [Science, Volume 205, 1,142–1,144 (1979); Biochim. Biophys. Acta, Volume 541, 321–333 (1979)].

SUMMARY OF THE INVENTION

Accordingly, it is an object of this invention to provide a process which overcomes these disadvantages and by which bilayer vesicles of a homogeneous size can be produced.

Upon further study of the specification and appended claims, further objects and advantages of this invention will become apparent to those skilled in the art.

These objects have been obtained by providing a process for producing bilayer vesicles from a colloidal solution comprising mixed micelles of a bilayer-forming substance and a detergent, the process comprising removing the detergent from the micelle-containing colloidal solution by means of flow-through dialysis whereby the colloidal solution is dialyzed against a dialysis liquid in a chamber formed at least partially by a semi-permeable membrane, wherein the dialysis liquid is moved along one side of a semi-permeable membrane at a velocity such that the detergent concentration in the dialysis liquid, on at least 90% of the active surface of the membrane, is at most 10% of the detergent concentration in the micelle solution in contact with the other side of the membrane, and wherein a homogeneous detergent concentration is maintained in the micelle solution by the movement of the latter.

BRIEF DESCRIPTION OF THE DRAWINGS

Various other objects, features and attendant advantages of the present invention will be more fully appreciated as the same becomes better understood when considered in conjunction with the accompanying drawings, in which like reference characters designate the same or similar parts throughout the several views, and wherein:

FIG. 1 shows a cross section through a dialysis cell and

FIG. 2 shows a front view of a side-wall element of the cell of FIG. 1.

DETAILED DISCUSSION

The removal of detergents from micelle solutions by means of known dialysis processes (e.g., by equilibrium dialysis, for example, by the dialysis bag method) leads to nonhomogeneous bilayer vesicles of various sizes and to multi-lamellar structures. It has been established that this is derived from the uncontrolled dialysis kinetics of the detergent. These nonuniform dialysis kinetics result from the fact that concentration gradients, which are constantly changing and, hence, cannot be controlled, build up both in the material to be dialyzed (the micelle solution) and also in the dialysate. This results in a constantly changing dialysis rate of the detergent, which can hardly be influenced, and which continuously changes the size distribution of the mixed micelles. The complete removal of the detergent from the micelle solution takes a very long time and exacerbates the above-mentioned disadvantages of the process.

To avoid uncontrollable changes in the concentration gradient transverse to the semi-permeable membrane, the process of this invention comprises moving the dialysis liquid, on at least one side of a semi-permeable membrane, at a velocity such that the detergent concentration in the dialysis liquid, on virtually the whole of the active surface of the membrane, in any case on at least 90% of this surface, is at most 10% of the detergent concentration in the micelle solution in contact with the other side of the membrane, and maintaining a homogeneous detergent concentration in the micelle solution by the movement, e.g., stirring, of the latter.

In this way, by keeping the detergent concentration in the dialysis liquid which is in contact with the membrane as low as possible at all points, preferably below about 2%, for example at about 1% or less, relative to the detergent concentration in the micelle solution, it is possible to ensure that, at all points on the active membrane surface, virtually identical concentration gradients are formed normal to the membrane surface. Homogeneous bilayer vesicles of a defined size, which can be used as carriers for biologically and pharmacodynamically active substances and/or can be employed as pharmaceutical preparations, are thereby obtained after a relatively short dialysis time.

Preferably, the dialysis liquid is carried past the semi-permeable membrane, with a constant flow velocity in laminar flow, in such a way that a linear concentration gradient of the detergent is formed from the entry of the dialysis liquid into the flow-through compartment up to its discharge as dialysate. In flow-through dialysis of this type, the intermediates resulting from the formation of the bilayer vesicles are already in themselves homogeneous and defined. The desired homogeneous bilayer vesicles of defined size are formed from these intermediates after removal of the detergent. The bilayer vesicle size can be controlled and selected conventionally by selection of the molar ratio of bilayer-forming substances/detergent in the initially formed colloidal solution, or by suitable choice of the detergent, or by choice of the dialysis kinetics of the detergent. Such dialysis kinetics, (i.e., dialysis rate) in turn depend, in a known manner, on the temperature, the ratio of membrane surface area/solution volume, the type of membrane (thickness, pore size), the concentration and the physical and chemical properties of the substances to be dialyzed. See, e.g., (a) "Membrane Separation Processes", P. Meares ed., chapter 1 and 2, p. 1–79, Elsevier Scientific Publ. Comp., New York (1979); (b) Biochemistry 18, 4173–4176 (1979) which disclosure is incorporated by reference herein.

A laminar flow of the dialysis liquid over the membrane surface has the advantage that the flow velocity can be kept approximately the same over the whole surface, and this is important since the flow velocity should be as high as possible, inter alia because of the desired low detergent concentration in the dialysis liquid, but a certain maximum, beyond which the molecular film on the membrane would be destroyed, of course, should not be exceeded. Preferably, the flow velocity of the dialysis liquid in the immediate vicinity of the membrane surface, at as many points as possible, is in the region of 0.2–6 m/minute, advantageously in the region of 1–3 m/minute.

The preferred laminar flow can be ensured, for example, by arranging, in the flow-through compartment, guide elements which are in contact with the membrane and which carry the dialysis liquid along the surface of the membrane in laminar flow. For example, the dialysis liquid can be carried over the surface of the membrane in a meandering or spiral channel in an element which is in contact with the membrane. Alternatively, it is also possible simply to construct the flow-through compartment with very low thickness (measured normal to the membrane), preferably a thickness of less than 1 mm. If this thickness is not more than about 2 mm and the dialysis liquid is introduced into the flow-through compartment, distributed over the width of the latter, an approximately laminar flow is likewise achieved at virtually all points.

The movement of the micelle solution in contact with the other side of the semi-permeable membrane, which movement is employed to maintain a homogeneous detergent concentration in the micelle solution, can be achieved, for example, by stirring with a mechanical stirring member (for example a magnetic stirring rod), or by forcing an inert gas into the chamber containing the micelle solution, or by moving the whole dialysis device to and fro (tilting movements) with this chamber.

The drawing shows a dialysis device with which an embodiment of the process of this invention can be carried out.

In the dialysis cell of FIGS. 1 and 2, two semipermeable membranes 1 are arranged between the ring 2 and, in each case, a side-wall element 3. A colloidal solution of mixed micelles is brought (e.g., through closable orifices in ring 2, which are not shown) into the interior space 4 between the two membranes 1.

The semi-permeable membranes must be impermeable to the bilayer-forming substances and to the aggregates or associates (e.g., the micelles, unilamellar or multilamellar vesicles) formed therefrom, but permeable to solvents and to auxiliaries and active substances dissolved therein. The following are particularly suitable as components of the membranes: cellulose, hydrated cellulose, regenerated cellulose (e.g., cellophane) as well as cellulose derivatives such as acetyl cellulose, furthermore polyamides, polyalkylenes such as polyethylene or polypropylene, polyesters, polyvinyl chloride, polytetrafluoroethylene, polycarbonates, etc.

The preferred membrane thickness is about 5 to about 20 μm.

The mixed micelles are produced from a detergent (solubilizer) and bilayer-forming substances.

Suitable micelle-forming solubilizers are nonionic, anionic, cationic or amphoteric detergents.

The following are particularly suitable as detergents: cholic acid, their salts and derivatives such as desoxycholic acid, taurocholic acid, chenodesoxycholic acid, lithocholic acid, glycocholic acid and their salts, preferably their sodium salts; glycosides, above all monomeric or oligomeric sugar derivatives with lipophilic side chain, e.g, 1-O-n-hexyl-β-D-glucopyranoside, 1-O-n-heptyl-β-D-glucopyranoside or 1-O-n-octyl-β-D-glucopyranoside.

Among the anionic solubilizers, there are suited in particular the Na and K salts of fatty acids of, preferably, 8 to 24 C atoms, amine soaps (e.g., triethanolamine stearate), salts of sulfuric and sulfonic acid esters of higher fatty alcohols such as sodium lauryl sulfate, docusate sodium salt or sodium lauryl sulfonate; among the cationic, quaternary ammonium compounds. Suitable nonionic solubilizers include, e.g., partial fatty acid esters of polyvalent alcohols such as glycerol monostearate, pentaerythritol monostearate; partial fatty acid esters of sorbitan (e.g., Span ®, Crill ®) and of polyoxyethylene sorbitan (e.g., Tween ®), reaction products of castor oil or hydrogenated castor oil with ethylene oxide (e.g., Cremophor ®EL), ethoxylated saturated fatty alcohols (e.g., cremophor ®A and O, Brij ®), polyethyleneglycol esters of fatty acids (e.g., Cremophor ®AP, Myrj ®), polyetheralcohols (e.g., Pluronic ®), etc.

Only amphiphilic substances which are capable of forming bilayers (i.e., double layers) in the aqueous phase can be used as bilayer-forming substances; that is, substances of polar (hydrophilic) as well as apolar (lipophilic) properties.

Suitable bilayer forming substances include, particularly, phospholipids, for instance phosphoglycerides (diesters, monoesters, diethers, monoethers wherein the ester and ether groups preferably are of 8 to 24 carbon atoms each) such as lecithins (phosphatidylcholines), kephalins (phosphatidyl-ethanolamines, phosphatidylserines), inositolphosphatides, phosphatidylic acids, phosphatidylglycerols, cardiolipin; sphingolipids, e.g., sphingomyelin; glycolipids, e.g., cerebrosides, gangliosides; furthermore, e.g., fatty acids of, preferably, 8 to 24 carbon atoms as well as their esters, salts and amides; alkyl ethers of, preferably 8 to 24 carbon atoms; alkyl ether derivatives of, preferably, 8 to 24 carbon atoms, such as 1,3-propanediol-phospholipids; higher alkylamines of, preferably, 8 to 24 carbon atoms, e.g., stearyl amine; fatty alcohols of preferably 8 to 24 carbon atoms, e.g., stearyl alcohol, higher alkylthiols of, preferably, 8 to 24 carbon atoms; etc. Furthermore, mixtures of these substances are also suitable. In general, the alkyl chains of the cited substances can be straight or branched.

The detergent and bilayer-forming substances form a ternary system with water, which is referred to here as a mixed micelle. The colloidal solution of the mixed micelle, which is subsequently called the micelle solution, can additionally contain electrolytes (predominantly physiologically compatible inorganic salts such as sodium chloride, sodium mono- and di-hydrogenphosphate, potassium mono- and di-hydrogenphosphate, etc.), sorption promoters (such as organic solvents, fatty alcohols and fatty acid esters, etc.), auxiliaries (such as stabilizers and preservatives), peptides, proteins, nucleic acids, lipids, antigens and antibodies, and also active substances with biological and pharmacodynamic properties, etc. Suitable active substances include, for instance, medicinally active compounds such as sterols, e.g., cholesterol, sitosterol, etc.; estrogens, e.g., estrone, estradiol and its esters, ethinylestradiol, etc.; gestagens, e.g., norethisterone acetate, chlormadinone acetate, etc.; corticoids, e.g., hydrocortisone, prednisolone, prednisone, dexamethasone, betamethasone, etc. and their esters, e.g., hydrocortisone acetate, betamethasone-17-valerate, etc.; antibiotics, e.g., penicillins, cephalosporins, aminoglysides such as gentamicin, etc.; antimycotics and dermatics, such as clotrimazol, miconazol, dithranol, benzoyl peroxide, etc.; antiphlogistics such as indometacin, methyl, benzyl or 2-butoxyethyl nicotinate, etc.; etc. Furthermore, cosmetically active agents are suitable, e.g., light protecting agents or agents for the care of the skin.

The micelle solution can contain about 5 to 150, preferably 10 to 100 mg/ml of bilayer-forming substance and about 1 to 200, preferably 5 to 100 mg/ml of detergent. Suitable concentrations of active substances and other mentioned micelle solution components may vary within broad limits; e.g., the active substances concentrations are usually 0.3 to 40, preferably 1 to 20 mg/ml. The concentration ranges for the other mentioned micelle solution components can also vary in these same ranges.

Suitably, the micelle solution is stirred, for example at about 75 rpm, in the interior space 4 of the dialysis cell by means of a magnetic stirring rod (which is not shown), in order to keep the detergent concentration virtually homogeneous.

Suitably, a dialysis liquid (the composition of which, generally, corresponds to that of the micelle solution except that the bilayer forming substance and the detergent are absent) is moved along the external sides of the membranes 1 in two flow-through compartments and with a sufficiently high velocity such that the detergent concentration in the dialysis liquid, which is built up by the detergent passing through the membranes, will remain below about 1% of the detergent concentration in the interior space 4 at virtually all points in this liquid and at all times (or for all dialysis detergent concentrations of this invention), in particular, including those where the liquid is in contact with the surfaces of the membranes 1 (=active membrane surfaces). In order to achieve this, it is advantageous to have a laminar flow of the dialysis liquid along the surfaces of the membranes 1. This laminar flow can be ensured by forming, in each of the side-wall elements 3, a meandering channel 5 through which the dialysis liquid must flow. The partitions 5a, between the mutually parallel sections of the channel, form flow-guiding elements for the dialysis liquid, which are in contact with the respective membrane 1. The dialysis liquid is introduced into the channel 5, at the bottom, through an inlet 6 in the side-wall element 3, and withdrawn from the channel 5, at the top, through an outlet 7. The average flow velocity in the channel 5 is advantageously between 20 and 600 cm/minute and preferably about 300 cm/minute, for a channel cross-section of, for example, about 1 mm$^2$ (width 2 mm, depth 0.5 mm).

Of course, it is also possible to use a spiral channel in place of the meandering channel 5. If desired, it is also possible to arrange several mutually parallel channels, separated from one another by partitions, between the inlet 6 and the outlet 7.

In certain cases, it is also possible to dispense with the carrying channel, i.e., to let the dialysis liquid flow on the external sides of the membranes through cylindrical flow-through compartments which are not interrupted by flow-guiding elements. In fact, in this case, in particular if the flow-through compartments are relatively thick, measured normal to the membranes, the results (uniformity of the vesicle size) are somewhat less good, but are still satisfactory, provided that it is ensured that the flow velocity of the dialysis liquid in the immediate vicinity of the membrane surface is in the region of 0.2–6 m/minute, preferably 1–3 m/minute, at virtually all points, and that there are virtually no regions with stagnating dialysis liquid, in which the detergent concentations could become too high.

Thus, homogeneous bilayer vesicles of defined size, which, if appropriate, can contain auxiliaries, peptides, proteins, nucleic acids, lipids, antigens or antibodies, or also active substances with biological and pharmacodynamic properties, are obtained in the interior space 4 after a relatively short dialysis time, (e.g., 1–3 hours), in the form of an aqueous dispersion. Depending on their solubility properties, these additives are encapsulated inside the bilayer vesicles and/or incorporated in the double layer and/or taken up on the outside of the double layer, whereupon the bilayer vesicles can be used, for example, as carriers for biologically and/or pharmacodynamically active substances and/or themselves constitute pharmaceutical preparations.

The dispersion obtained contains about 5 to 150, preferably 10 to 100 mg/ml of the bilayer forming substance and, if desired, up to 40, preferably up to 20 mg/ml of the active substance. If desired, an obtained dilute dispersion can also be concentrated, e.g., by partial evaporation or by partical lyophilization, suitably up to a concentration of about 150, preferably about 100 mg/ml of the bilayer forming substance only, however.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLES OF A PREPARATION

Example 1

65 mg of egg lecithin in ethanolic solution are evaporated to dryness and the residue is resuspended in 5 ml of 1 mM phosphate buffer (composed of Na$_2$HPO$_4$.2-H$_2$O, KH$_2$PO$_4$ and 0.9% NaCl) of pH 7.3 and ionic strength 0.16. 58.3 mg of solid sodium cholate are added to this suspension, while stirring constantly, and the mixture is left to stand for two minutes at room temperature under a nitrogen atmosphere, until the formation of the mixed micelles is complete (the micelle solution becomes clear). To remove the sodium cholate, the micelle solution is subjected at room temperature, to the flow-through dialysis system described in FIGS. 1 and 2, the micelle solution being stirred constantly (75 rpm). Cellulose membranes with a molecular exclusion limit of about 10,000 are used as the dialysis membranes. The flow rate of the dialysate is about 3 ml/minute in each side-wall element 3. Bilayer vesicles are obtained after a dialysis time of 20-24 hours, the residual cholate contents of which are less than 1%, relative to the initial cholate content. Bilayer vesicles produced under these conditions are homogeneous and have a diameter of 60±3 nm. The comprehensive physicochemical characterization of these vesicles is described in Biochim. Biophys. Acta. 512, 147-155 (1978).

Examples 2 to 17

The size of the bilayer vesicles can be influenced, for example, by using dialysis membranes with different permeation properties, and/or by varying the bilayer-forming substances, and/or by varying the molar ratio of bilayer-forming substances/detergent, and/or by selection of detergent. Results are summarized in the following table.

able for therapeutic administration, and, if appropriate, the mixture is converted to a particular galenic form.

The following galenic forms of administration are possible:

ampoules, in particular sterile injection and infusion solutions, the colloidal solution of the bilayer vesicles containing pharmacodynamically active substances being subjected to an antimicrobial treatment;

solutions, in particular syrups, eye drops and nose drops, which can contain diverse auxiliaries in addition to the bilayer vesicle solution described above;

non-metering aerosols and metering aerosols, which can contain propellent gas and stabilizers in addition to the bilayer vesicle solution described above;

emulsions, such as water-in-oil or oil-in-water emulsions, for parenteral, oral and topical, (e.g., creams) administration, and also emulsions of these types which have been processed to give corresponding nonmetering aerosols or metering aerosols. Water-in-oil emulsions form, for example, the contents of soft gelatin capsules which can be administered perorally or rectally.

Furthermore, gels and the most recently developed therapeutic systems based on diffusion, osmotic and soluble units, such as, for example, Ocusert ®, Biograviplan ®, the displacement pump Alzet ®, and Oros (oral therapeutic system), can also be used as possible forms of administration, which again comprise the colloidal solutions of the bilayer vesicles containing pharmacodynamically active substances.

Bilayer vesicles in the lyophilized state can be pro-

| Example No. | Molecular exclusion Limit of dialysis membrane | Bilayer-forming substance or lipid mixture, respectively (Molar ratio) | Detergent | Molar ratio: bilayer-forming substance (or lipid mixture, respectively)/ detergent | Temperature °C. | Diameter of bilayer vesicles in nm |
|---|---|---|---|---|---|---|
| 2 | 2000 | EL | NaC | 0.625 | 20 | 75 |
| 3 | 10000 | EL/10% PA | NaC | 0.625 | 20 | 50 |
| 4 | 10000 | EL/20% PA | NaC | 0.625 | 20 | 40 |
| 5 | 10000 | EL | NaC | 0.60 | 20 | 54 |
| 6 | 10000 | EL | NaC | 0.95 | 20 | 69 |
| 7 | 10000 | EL | NaC | 1.15 | 20 | 80 |
| 8 | 10000 | EL | OG | 0.18 | 20 | 170 |
| 9 | 10000 | EL/cholesterol (8:2) | NaC | 0.60 | 20 | 80 |
| 10 | 10000 | EL/cholesterol (7:3) | NaC | 0.52 | 20 | 61 |
| 11 | 10000 | EL/phosphatidyl-ethanolamine (3:7) | NaC | 0.22 | 20 | 36 |
| 12 | 10000 | EL/phosphatidyl-inositol (8:2) | NaC | 0.60 | 20 | 60 |
| 13 | 10000 | EL/phosphatidic acid (10:2) | NaC | 0.62 | 20 | 42 |
| 14 | 10000 | EL/stearylamine (10:2) | NaC | 0.62 | 20 | 49 |
| 15 | 10000 | bovine brain cerebroside/ EL (100 g/mol) | NaC | 0.60 | 20 | 81 |
| 16 | 10000 | dimyristoylphosphatidylcholine/phosphatidylinositol (10:2) | NaC | 1.25 | 30 | 143 |
| 17 | 10000 | EL | OG | 0.20 | 20 | 177 |

EL = egg lecithin
PA = phosphatidic acid from egg lecithin
NaC = sodium cholate
OG = n-octyl-β-D-glucopyranoside The bilayer vesicles of defined size, produced in accordance with the process described, can be used as carriers for biologically and pharmacodynamically active substances and/or can be employed as a pharmaceutical preparation. Pharmaceutical preparations can thus be produced in such a way that the bilayer vesicles are mixed as the active constituent, with a carrier suitable for therapeutic administration, together with corresponding pharmaceutical auxiliaries to give tablets or dragees.

Example of an Application: Hydrogel (a) In analogy to Example 1, 320 mg of egg lecithin, 80 mg of cholesterol and 40 mg of betamethasone 17-valerate are dissolved in ethanol. The solution is evaporated to dryness, the residue is resuspended in 20 ml of phosphate buffer, and 400 mg of sodium cholate is added. Thereafter, the procedure of Example 1 is followed.

(b) In 75 ml of water, there are dissolved 0.2 g of potassium sorbate, 0.224 g of $Na_2HPO_4.12H_2O$ and 0.64 g of $KH_2PO_4$. With light warming and vigorous stirring, 2 g of hydroxyethyl cellulose is dissolved in the solution obtained. After 0.5 hour of standing, 2 g of glycerol is added with stirring, followed by the liposome dispersion obtained according to (a). The volume of the mixture is adjusted to 100 ml by adding water.

The obtained hydrogel contains 0.04% of active substance and shows a pH value of 5.8 to 6.3.

The preceding examples can be repeated with similar success by substituting the generically or specifically described reactants and/or operating conditions of this invention for those used in the preceding examples.

From the foregoing description, one skilled in the art can easily ascertain the essential charcteristics of this invention, and without departing from the spirit and scope thereof, can make various changes and modifications of the invention to adapt it to various usages and conditions.

What is claimed is:

1. A process for producing unilamellar bilayer vesicles of substantially homogeneous size from a colloidal solution comprising mixed micelles of a bilayer-forming substance and a detergent, the process comprising removing the detergent from the micelle-containing colloidal solution by means of flow-through dialysis whereby the colloidal solution is dialyzed against a dialysis liquid in a chamber whose walls are at least partially formed by a semi-permeable membrane, wherein the dialysis liquid is moved along the outer side of the semi-permeable membrane in laminar flow in at least one channel at a sufficient velocity to ensure that the detergent concentation in the dialysis liquid, on at least 90% of the active surface of the membrane, is at most 10% of the detergent concentration in the micelle solution in contact with the other side of the membrane, and wherein a homogeneous detergent concentration is maintained in the micelle solution by the movement of the latter.

2. A process of claim 1, wherein the velocity of the dialysis liquid is chosen such that the detergent concentration in the dialysis liquid is at most 2% of the detergent concentration in the micelle solution.

3. A process of claim 1, wherein the velocity of the dialysis liquid is chosen such that the detergent concentration in the dialysis liquid is at most 1% of the detergent concentration in the micelle solution.

4. A process of claim 1, wherein the channel is a meandering channel.

5. A process of claim 1, wherein the channel is a spiral channel.

6. A process of claim 1, wherein the colloidal solution of the mixed micelles further comprises at least one of the following additives: an electrolyte, a sorption promoter, an auxiliary, a peptide, a protein, a nucleic acid, a lipid, an antigen, an antibody or a biologically or pharmacodynamically active material.

7. A dialysis device for carrying out the process of claim 1, comprising a chamber (4) for the micelle solution, the walls of said chamber being at least partially formed of a semi-permeable membrane; means for moving the micelle solution in the chamber; at least one flow-through compartment for the dialysis liquid, which compartment has an inlet and an outlet for the dialysis liquid and is separated from the chamber (4) by a semi-permeable membrane (1); continuous guide elements (5a) in contact with the membrane (1) and arranged in the flow-through compartment such that the dialysis liquid can be moved along the surface of the membrane (1) in a laminar flow, said guide elements forming at least one channel which is in contact with the active surface of the membrane and extends continuously therealong from said inlet to said outlet and within which the dialysis liquid is guided along said membrane.

* * * * *